(12) United States Patent
Dauster et al.

(10) Patent No.: US 8,211,111 B2
(45) Date of Patent: Jul. 3, 2012

(54) SPINAL ROD MANIPULATOR INSTRUMENT

(75) Inventors: Andrew Dauster, Breinigsville, PA (US); Matthew Kovach, Steamboat Springs, CO (US); Paul Weaver, Douglassville, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 628 days.

(21) Appl. No.: 12/397,807

(22) Filed: Mar. 4, 2009

(65) Prior Publication Data

US 2010/0228302 A1 Sep. 9, 2010

(51) Int. Cl.
*A61B 17/70* (2006.01)
(52) U.S. Cl. ...................................... 606/86 A

(58) Field of Classification Search ............... 606/86 A, 606/86 B, 86 R, 246–279
See application file for complete search history.

(56) References Cited

U.S. PATENT DOCUMENTS

| 6,036,692 A | 3/2000 | Burel et al. | |
|---|---|---|---|
| 2008/0234765 A1* | 9/2008 | Frasier et al. | 606/86 A |
| 2010/0185242 A1* | 7/2010 | Barry et al. | 606/279 |
| 2010/0185248 A1* | 7/2010 | Barry et al. | 606/86 A |

* cited by examiner

*Primary Examiner* — Eduardo C Robert
*Assistant Examiner* — Summer Kostelnik
(74) *Attorney, Agent, or Firm* — RatnerPrestia

(57) ABSTRACT

An instrument for manipulating a spinal fixation rod includes a gripping section for engaging a spinal implant and a lever body pivotally attached to the gripping section. A rod carrier extends from one side of the lever body and is adapted to push a spinal fixation rod downwardly into the spinal implant.

20 Claims, 6 Drawing Sheets

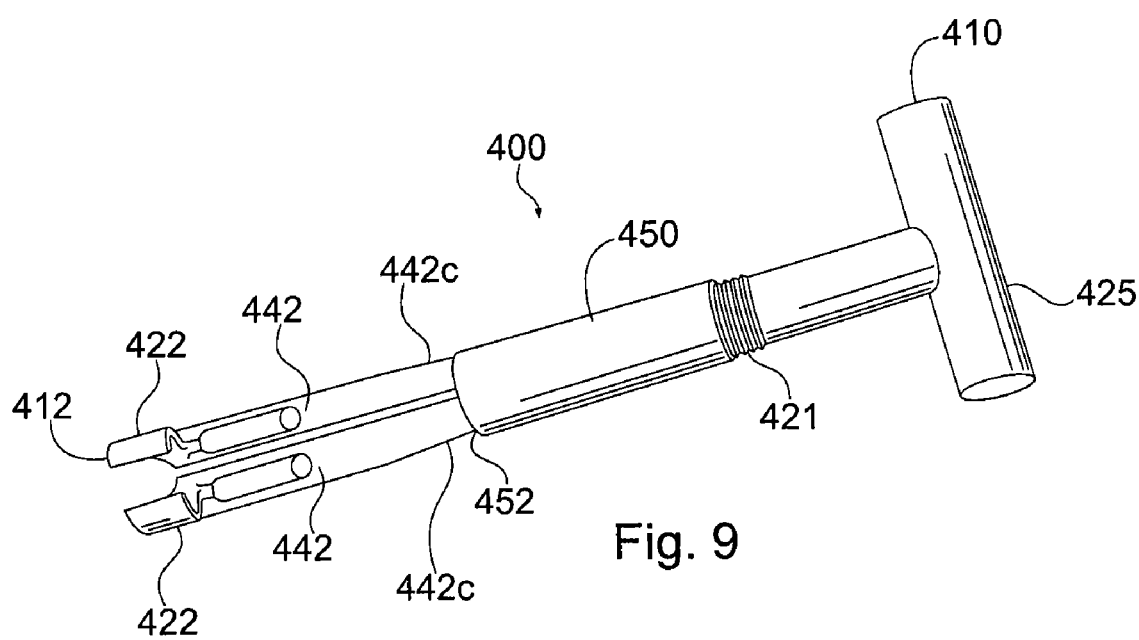

SPINAL ROD MANIPULATOR INSTRUMENT

FIELD OF THE INVENTION

The present invention is related generally to instrumentation for manipulating spinal fixation rods, and more specifically to an instrument for advancing a spinal fixation rod into a receiver body implanted in bone.

BACKGROUND

In many spinal fixation systems, a spinal rod is used to correct and stabilize the spine, so that fusion can be achieved at selected levels in the spine. The spinal rod is attached to the spine by a series of screw or hook implants, with each implant attached to a vertebral body. Typically, each implant includes a head portion, sometimes called a "rod receiver" or "saddle", that forms a channel. The rod rests inside the channels and interconnects the implants to one another. A locking element, such as a set screw, is inserted into each channel and over the rod to lock the rod in place in the channel. The rod is thereby supported by multiple implants that are secured to the rod at multiple locations.

In many instances, the rod does not align precisely with all of the saddles during insertion. One common reason for this is that the implants and their channels are seldom arranged relative to one another in a perfectly straight line. More often, the implants are positioned in a non-linear arrangement due to the curvature of the spine and the relative positions of the vertebrae. As a result, when one section of a rod is locked down in one implant, another section may extend above the next implant, outside the channel. For example, after a first section of a rod is locked in place in one saddle, a second section of the rod may extend partially outside or entirely outside the channel in the next adjacent saddle. This is particularly common when the receiver bodies are small, with relatively short channels. When this happens, the second section of rod must be pushed down into the saddle until it is reaches a sufficient depth within the channel to provide room for a set screw above the rod. A rod persuader instrument may be used in such cases to advance the second section of the rod down into the channel, so that a set screw or other fastener can be inserted into the saddle over the rod.

Rod persuader instruments that are used to perform rod reduction must apply sufficient downward force on the rod to position the rod in the saddle portion of the implant. To provide such force, many rod persuader instruments are designed to attach directly over the opening in the saddle. This attachment can be difficult, especially when the rod receiver body has a relatively short profile length. When the rod receiver body has a relatively short length, there is little or no surface area for gripping by a rod persuader.

Another drawback with instruments that attach over the top of a rod receiver body is limited visibility. Rod persuader instruments that attach over top of a receiver body can visually obstruct the opening in the saddle, and the surgeon can not see down into the channel. This can make it difficult to introduce a set screw into the saddle.

In view of the foregoing, many known rod persuader instruments leave much to be desired in terms of function and operation.

SUMMARY OF THE INVENTION

In a first aspect of the invention, an instrument for manipulating a spinal fixation rod includes a gripping section for engaging a spinal implant and a lever body. The lever body is pivotally attached to the gripping section, and a rod carrier extends from the lever body. The gripping section extends from a first side of the lever body, and the rod carrier extends from a second side of the lever body.

In a second aspect of the invention, an instrument for manipulating a spinal fixation rod includes a gripping section for engaging a spinal implant and a lever body. The lever body is pivotally attached to the gripping section, and a rod carrier extends from the lever body. The lever body includes a first lever arm and a second lever arm separated from the first lever arm by a gap. The gripping section includes a first gripping extension pivotally coupled with the first lever arm, and a second gripping extension pivotally coupled with the second lever arm.

In a third aspect of the invention, an instrument for manipulating a spinal fixation rod includes a gripping section for engaging a spinal implant and a lever body. The lever body is pivotally attached to the gripping section, and a rod carrier extends from the lever body. A handle end is operable to displace the gripping section between an open position and a closed position. The handle end is also operable to pivot the lever body relative to the gripping section.

BRIEF DESCRIPTION OF THE DRAWINGS

The foregoing summary and the following description will be better understood in conjunction with the drawing figures, of which:

FIG. 9 is a perspective view of an instrument in accordance with an alternate embodiment of the invention.

DETAILED DESCRIPTION OF EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
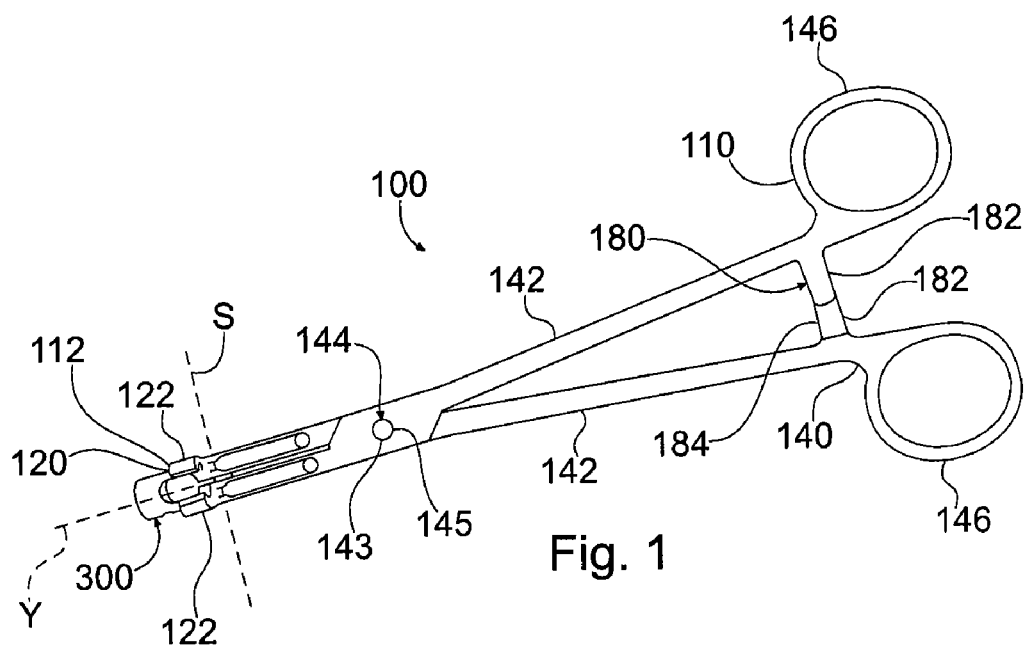
FIG. 1 is a perspective view of an instrument in accordance with one exemplary embodiment of the invention, shown engaged with an implant component.
Figure 2:
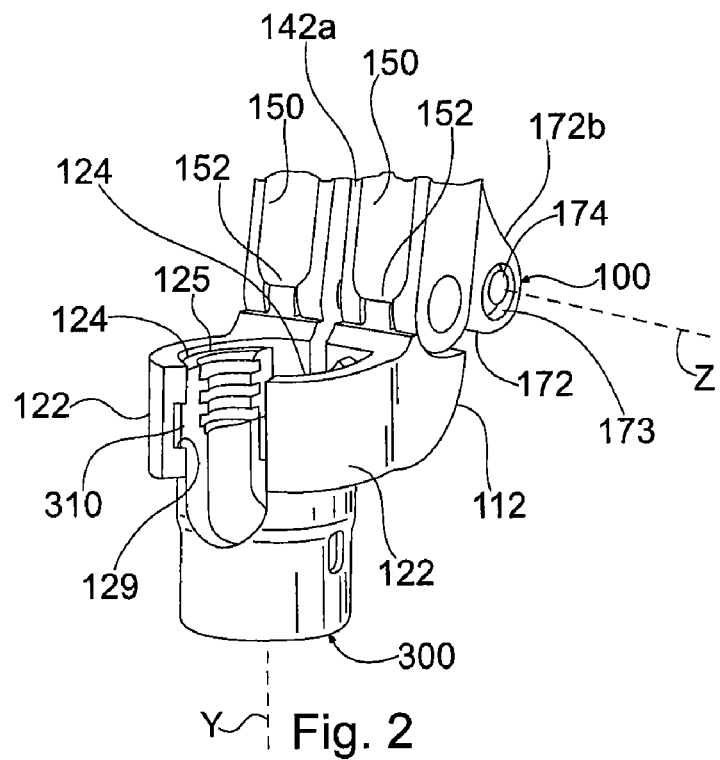
FIG. 2 is an enlarged perspective view of the distal end of the instrument and implant component of FIG. 1, truncated for clarity.
Figure 3:
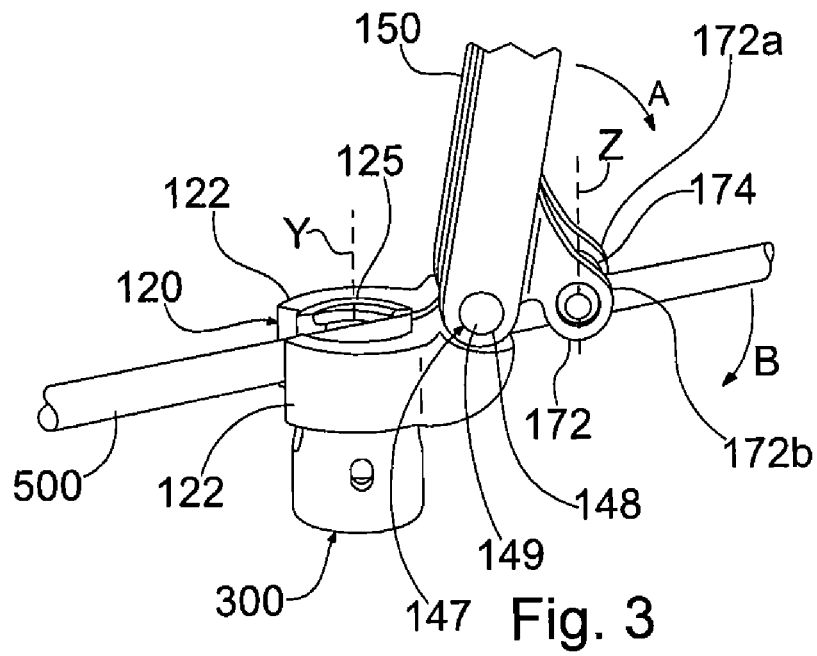
FIG. 3 is another enlarged perspective view of the distal end of the instrument and implant component of FIG. 1, truncated for clarity, shown with a spinal fixation rod in a first position.

Referring to FIGS. 1 and 2, an instrument 100 for manipulating a spinal fixation rod is shown in accordance with one exemplary embodiment of the invention. Instrument 100 is designed to advance a spinal fixation rod into a rod receiving component on a spinal implant, without blocking access to the top opening of the rod receiver component. In particular, instrument 100 engages only one side of a rod receiver component, and advances a rod downwardly into a seated position in the rod receiver component without obstructing the top opening of the rod receiver component. Unlike many conventional rod persuaders, instrument 100 acts on and applies force to a spinal rod at a rod section located outside of the receiver body, not a section that is to be inserted in the receiver body. This allows the instrument to move the rod and subsequently hold down the rod, while keeping the top opening clear and unobstructed to receive a fastener over top of the rod. By applying force to the rod outside of the receiver body, rather then above or inside the channel, instrument 100 can be used to adjust rods when one end or section is elevated, as shown in FIG. 3. Instrument 100 has a proximal end 110 and a distal end 112 opposite the proximal end. The term "proximal", as used in this application, refers to a direction with respect to the instrument that is oriented toward the user when the instrument is in use. The term, "distal", as used in this application, refers to a direction with respect to the instrument that is oriented toward the patient when the instrument is in use. As such, proximal end 110 is the end of the instrument oriented toward the surgeon when the instrument is in use, and distal end 112 is the end of the instrument engaging or oriented toward the patient when the instrument is in use.

Instruments in accordance with the invention include a gripping mechanism for engaging a spinal implant. The gripping mechanism may incorporate a variety of configurations for securely engaging an implant, including configurations that conform to the exterior of the implant. Distal end 112 of instrument 100, for example, includes a gripping end 120 that features a pair of clamping extensions 122. Clamping extensions 122 are movable towards one another and away from one another, analogous to forceps. Within this range of motion, clamping extensions 122 are movable between an open position, in which the clamping extensions are spread apart, and a closed position, in which the clamping extensions are brought together in a more or less adjacent arrangement. The closed position is shown in FIGS. 1 and 2.

Each clamping extension 122 has an arc-shaped inner surface 124. Inner surfaces 124 are symmetrically arranged and form a generally cylindrical passage 125 when clamping extensions 122 are brought together. With this configuration, clamping extensions 122 can be manipulated to engage and clamp onto the exterior of an implant with one or more curved perimeter edges, such as a cylindrical implant. In FIGS. 1 and 2, for example, clamping extensions 122 are shown in clamping engagement with a cylindrical rod receiver body 300. Cylindrical passage 125 has a longitudinal axis Y that generally aligns with the longitudinal axis of rod receiver body 300.

Instruments in accordance with the invention may utilize a number of different mechanisms for operating gripping end 120, including but not limited to forceps handles, tong configurations or telescoping sleeves. In instrument 100, for example, proximal end 110 includes a handle end 140 that operates the clamping extensions 122 in a hinged articulating arrangement. In particular, handle end 140 is operable to move the clamping extensions 122 between the open and closed positions. Handle end 140 includes a pair of arms 142 connected by a hinge 144 in a pivoting arrangement. Arms 142 include bores 143 that align coaxially with one another and receive a hinge pin 145. The proximal end of each arm 142 includes a finger loop 146. Finger loops 146 are operable similar to a forceps handle to move clamping extensions 122 between the open and closed positions. More specifically, finger loops 146 are movable toward one another in a closed arrangement to bring clamping extensions 122 to the closed position (shown in FIG. 1), and away from one another in an open arrangement to move the clamping extensions to the open position.

Arms 142 are separately and independently movable with respect to each other in a first plane to open and close clamping extensions. This first plane passes through both arms 142 and finger loops 146, generally perpendicular to the axis of pin 145. Arms 142 also pivot in unison with respect to clamping extensions 122 along a pivot axis "S" at their distal ends. The pivot direction is represented schematically by arrow "A" in FIG. 3. Each arm 142 is pivotally connected to one of the clamping extensions 122 by a hinge 147. The distal ends of arms 142 include bores 148 that align coaxially with each other and receive separate lever pins 149.

Figure 4:
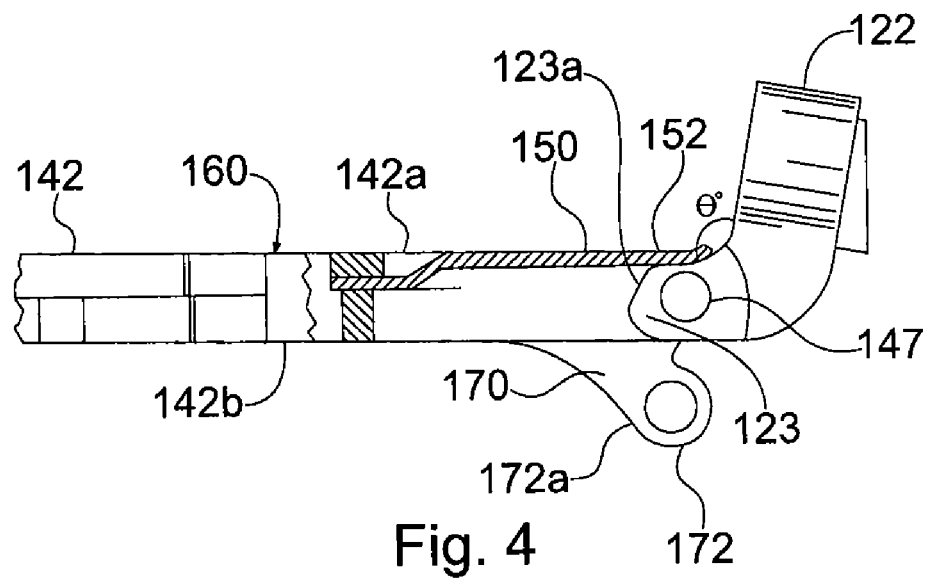
FIG. 4 is a side elevation view of the distal end of the instrument and implant component of FIG. 1, truncated for clarity.
Figure 5:
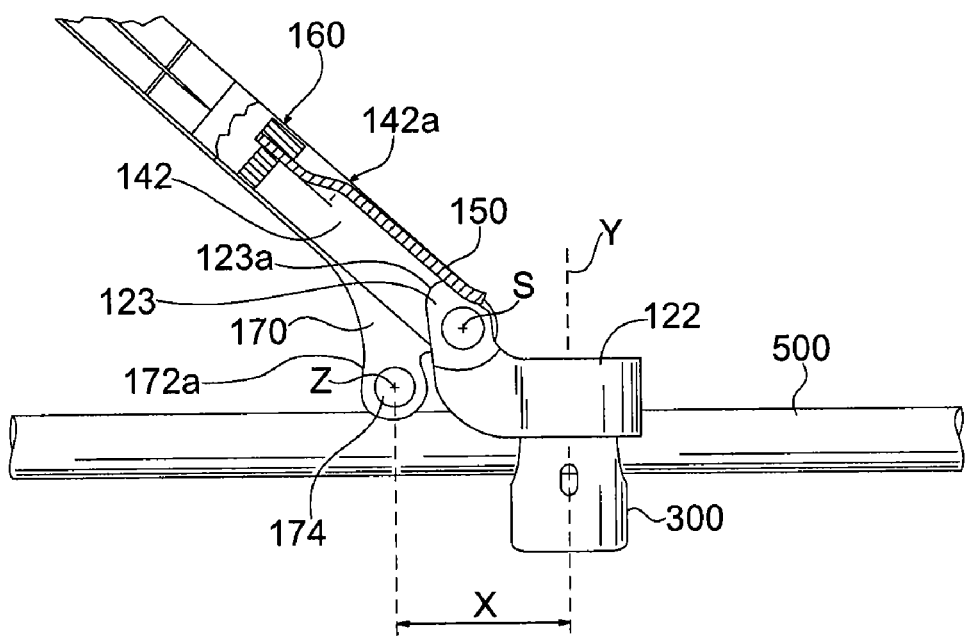
FIG. 5 is a side elevation view of the distal end of the instrument, implant component and spinal fixation rod of FIG. 3, truncated for clarity, shown with the spinal fixation rod moved to a second position, and a portion of the instrument broken away to show elements and features inside the instrument.

In a preferred embodiment, arms 142 incorporate a self-aligning mechanism that maintains clamping extensions 122 together in parallel and symmetrical alignment, and at the same angle relative to the arms. Referring to FIGS. 2, 4 and 5, each arm 142 includes a built-in biasing element in the form of a leaf spring 150 on a first side 142a of the arm. Each leaf spring 150 has a distal end 152 that engages one of the clamping extensions 122. Each clamping extension 122 has a proximal section 123 with a camming surface 123a that engages the adjacent leaf spring 150. Leaf springs 150 are deflected outwardly by the camming surfaces 123a as the angle Θ between arms 142 and clamping extensions 122 is increased. That is, when force is applied to arms 142 to pivot the arms away from clamping extensions 122, camming surfaces 123a engage and deflect leaf springs 150 outwardly, as shown in FIG. 5. Leaf springs 150 are configured to return back to a relaxed condition, such as that shown in FIG. 4, after the force is removed from arms 142. Because leaf springs 150 remain parallel to one another and remain in constant engagement with clamping extensions 122, the leaf springs keep the clamping extensions aligned with one another at the same angle relative to arms 142, so that they can be easily aligned with and attached to an implant.

Arms 142 operate in unison, acting as parts of a single lever body 160 during pivot motion about axis "S". That is, arms 142 pivot in unison relative to clamping extensions 122. The distal end of lever body 160 includes a rod carrier 170 with a pair of supports 172. Each support 172 extends from a second side 142b of its associated arm 142. Second sides 142b of arms 142 are opposite first sides 142a, so that supports 172 extend outwardly from the arms in a direction opposite the direction of clamping extensions 122. A cross bar 174 extends between supports 172 and has a cross bar axis Z, shown in FIG. 5, that extends generally parallel to axis S and generally perpendicularly to axis Y. Cross bar 174 straddles the space between arms 142 and is positioned to contact a spinal rod as lever arm 160 is pivoted downwardly.

Figure 6:
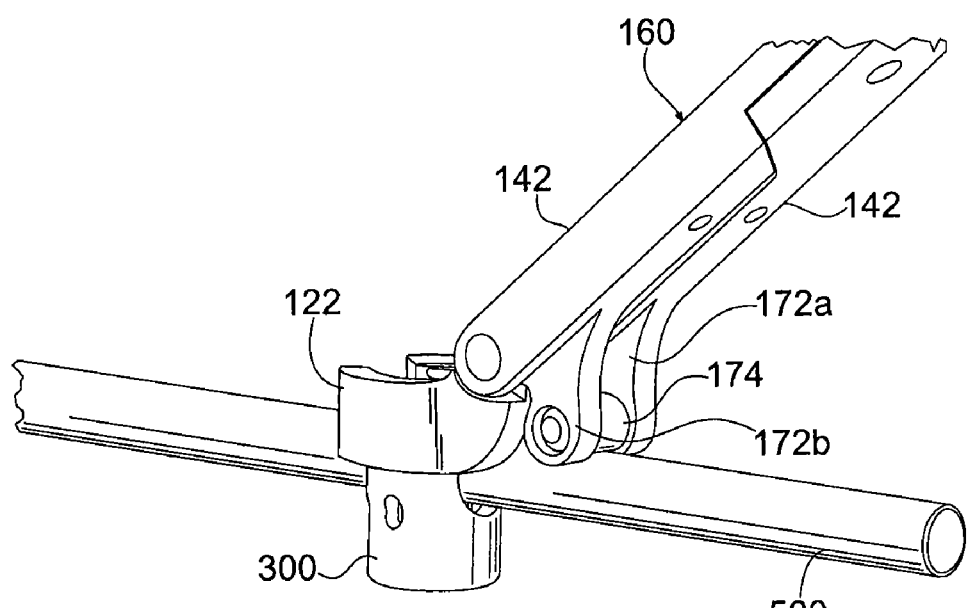
FIG. 6 is a perspective view of the distal end of the instrument, implant component and spinal fixation rod of FIG. 5, truncated for clarity.
Figure 7:
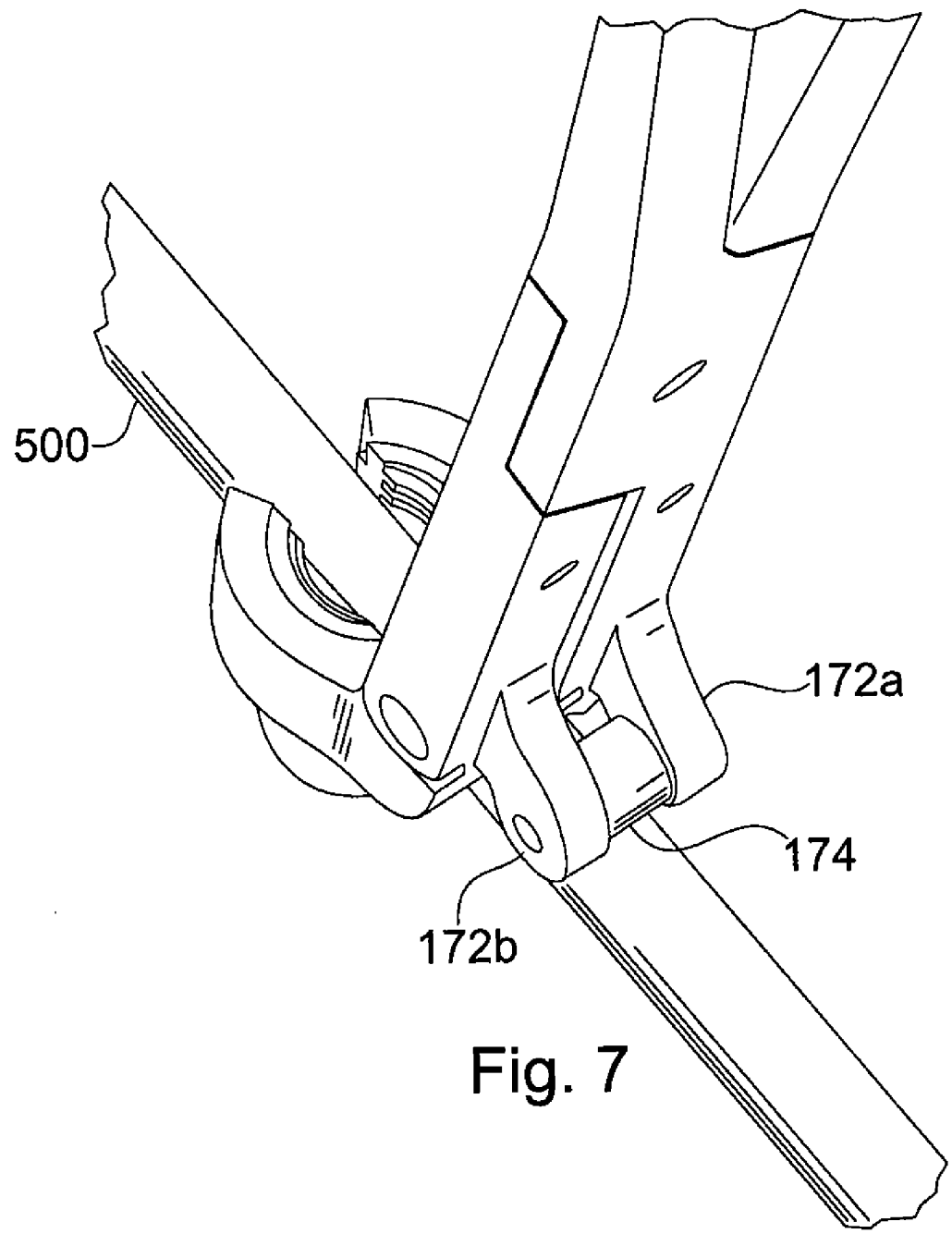
FIG. 7 is a perspective view of the distal end of the instrument, implant component and spinal fixation rod of FIG. 5, truncated for clarity.

Referring again to FIG. 3, instrument 100 is shown in the process of advancing a spinal rod 500 downwardly into rod receiver 300. Cross bar 174 is designed to engage a top edge of spinal rod 500 as shown, and push the rod down inside the channel of rod receiver 300 as lever arm 160 is pivoted. These dynamics are illustrated schematically by arrows "A" and "B". As lever arm is pivoted in direction A, for example, rod 500 is advanced downwardly in direction B. FIGS. 5 and 6 show instrument 100 after it has advanced rod 500 downwardly into the channel of rod receiver 300. Cross bar axis Z is offset from axis Y of clamping extensions 122 by a distance X. Distance X changes as lever arm 160 is pivoted relative to an engaged implant. Cross bar 174 may have a number of different longitudinal profiles. For example, cross bar 174 may have a cylindrical profile with a uniform diameter, or may be tapered to a narrower diameter at a midpoint along the cross bar, similar to an hourglass shape, to keep the cross bar more or less centered over the rod. Referring to FIGS. 6 and 7, cross bar 174 has a cylindrical profile.

Rod carriers in accordance with the invention can be constructed in a number of ways. For example, the cross bar may be formed by a pair of cantilevered sections that extend toward one another from each support arm and abut end to end when the clamping extensions are closed. Alternatively, the cross bar may be formed by a single bar extending from one support arm. Cross bar 174, for example, is attached to one of the supports 172a, and is received by the other support 172b when the clamping extensions 122 are moved to the closed position. Support 172a, which is attached to the cross bar, i.e. the "base support", is fixed to a first end of the cross bar by laser welding or other fixed connection. Support 172b that receives the cross bar 174, i.e. the "receiving support", has a bore 173 with a diameter sized to receive cross bar 174 when the arms 142 are closed together. When arms 142 are moved away from one another, such as when clamping extensions 122 are opened, cross bar 174 is drawn at least partially out of bore 173 of receiving support 172b.

Figure 8:
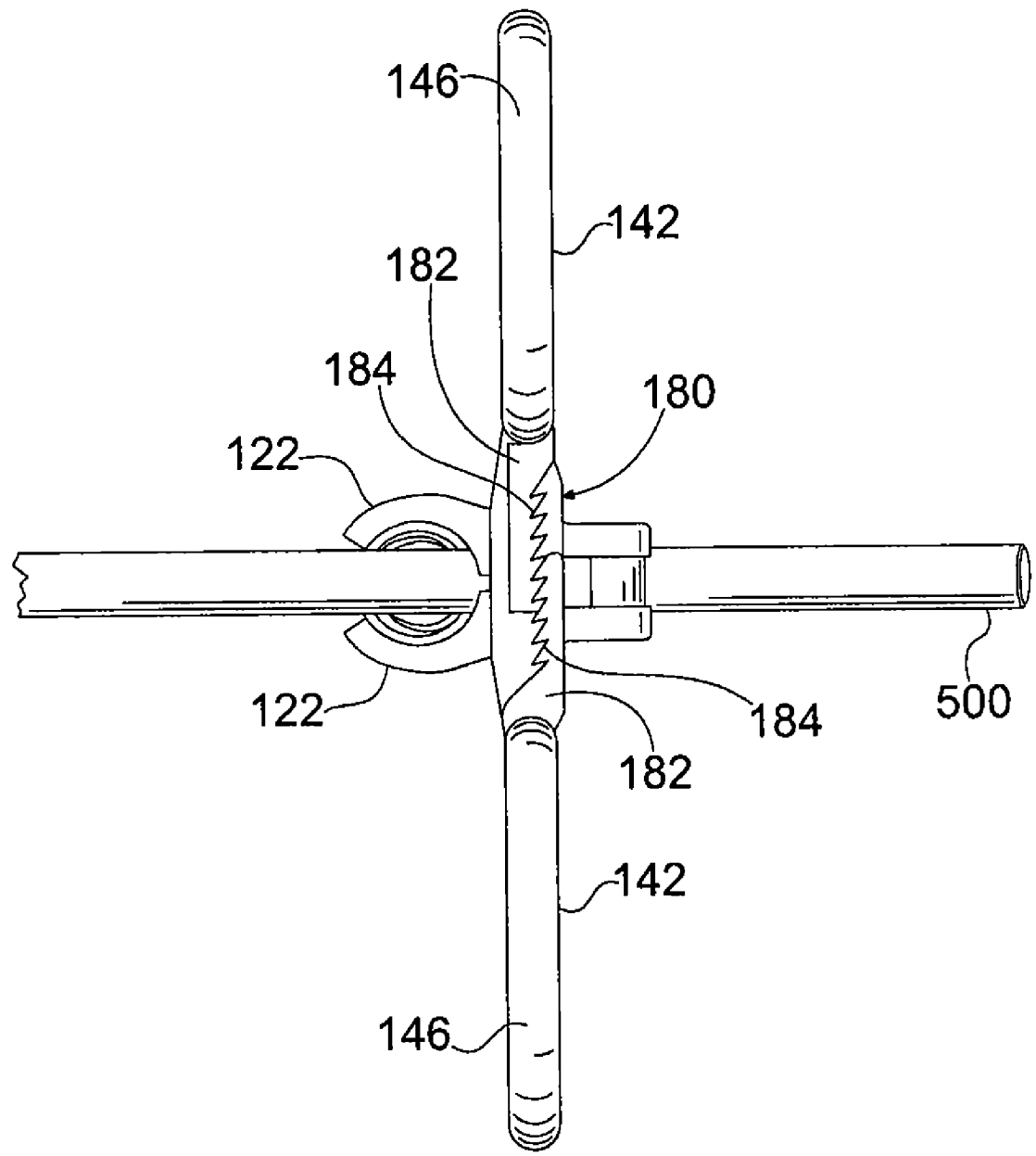
FIG. 8 is a top view of the instrument, implant component and spinal fixation rod of FIG. 5, truncated for clarity.

In preferred embodiments, the instrument includes a locking mechanism to maintain the gripping section in a securely engaged position around a rod receiver body. For example, instrument 100 includes a ratchet lock 180 between arms 142, as shown in FIGS. 1 and 8. Ratchet lock 180 includes a pair of opposing rails 182 with opposing sets of ratchet teeth 184. The sets of ratchet teeth 184 face one another and engage each other. The geometry of ratchet teeth 184 allows slidable engagement of rails 182 in one direction while the rails are mated against one another. More specifically, teeth 184 allow the rails to slide against one another as arms 142 are pressed toward one another. Teeth 184 have flat sides that prevent or at least resist sliding motion in the opposite direction, so as to prevent or limit arms 142 from being expanded or separated away from one another. With this limited sliding arrangement, handle arms 142 can be squeezed together to close clamping extensions 122, and held in the closed condition to maintain a clamping force on the rod receiver body 300. Outward movement of clamping extensions 122 is prevented or limited due to the engagement of ratchet teeth 184. Once clamping extensions 122 are closed, the clamping extensions can be opened by releasing ratchet teeth 184 and rails 182 from one another. Ratchet teeth 184 can be released with a number of optional design features. For example, one or both rails 182 can be flexibly connected to arms 142, allowing one or both rails to be bent or flexed out of engagement when it is time to open the clamping extensions 122. Alternatively, arms 142 may have a limited degree of freedom to slide along the axis of hinge 147, so that the arms can be separated from one another and disengage the sets of ratchet teeth 184 from each other. Another option is to provide a relatively smooth contour on the ratchet teeth. Under this option, the ratchet teeth provide limited resistance against opening the arms, but the smooth contour on ratchet teeth permit the teeth to slide in the reverse direction when a moderate amount of force is applied by the user to spread the finger loops 146 apart from one another.

Clamping extensions in accordance with the invention may include a number of internal or external surface geometries to facilitate engagement with a rod receiver component. Referring again to FIG. 2, for example, inner surfaces 124 of clamping extensions 122 each include a channel 129 for receiving a flange 310 on the exterior of receiver body 300. The engagement between flanges 310 and channels 129 substantially limits or prevents movement of clamping extensions 122 relative to receiver body 300. The channels inside the clamping extensions may be generally linear so that the clamping extensions engage a receiver body in a normal orientation, such as that shown in FIG. 2, and remain fixed in that relationship with the receiver body. Alternatively, the channels may have an irregular shape that allows a limited range of tilting or rocking motion of the clamping extensions with respect to the receiver body.

Instruments in accordance with the invention can use mechanisms other than forceps-style handles to open and close the clamping extensions. Referring to FIG. 9, an alternate instrument 400 is shown in accordance with the invention. Instrument 400 has many aspects in common with instrument 100, including a proximal end 410, a distal end 412 with a pair of arms 442, and a pair of self-aligning clamping extensions 422. Instead of a forceps-style handle, instrument 400 has a T-shaped handle 425 and a collar 450. Collar 450 surrounds arms 442, and has an inner wall 452 that engages the exterior of the arms. Side edges 442c of arms 442 taper outwardly by a small angle as they extend distally, so that the pair of arms become gradually wider toward the distal end. Collar 450 is axially displaceable along the length of the arms to adjust the relative position of clamping extensions 422. As collar 450 is advanced over arms 422 toward distal end 412, inner wall 452 of the collar gradually bears against the arms (which become wider toward the distal end) and squeezes the arms toward one another. As collar 450 is moved toward a proximal end 410 of instrument 400, the collar gradually releases arms 422 and allows them to spread apart. In this arrangement, collar 450 can be advanced toward the distal end 412 to close clamping extensions 422, and drawn back toward proximal end 410 to open the clamping extensions.

Movement of collar 450 is preferably limited, and may be controlled using a number of attachment mechanisms and stops. In the illustrated embodiment, for example, collar 450 includes an internal thread that engages an external thread 421 on a shaft portion 426 of T-shaped handle 425. With a threaded arrangement, collar 450 is movable over arms 422 by rotating the collar relative to T-handle 425. Alternatively, collar 450 may simply slide freely over arms 422. Flanges, tabs or other protrusions extending radially outwardly from shaft 426 may be provided to engage internal rims or stops inside collar 450 to limit the range of axial displacement of collar.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An instrument for manipulating a spinal fixation rod, the instrument comprising:
 a gripping section for engaging a spinal implant;
 a lever body pivotally attached to the gripping section on a pivot axis, the lever body comprising a first side and a second side opposite the first side; and
 a rod carrier extending from the lever body, the gripping section extending from the first side of the lever body, and the rod carrier extending from the second side of the lever body, the rod carrier comprising a first support extending outwardly from the second side of the lever body and a second support extending outwardly from the second side of the lever body generally parallel to the first support, the first support comprising a cross bar having a longitudinal cross bar axis extending generally parallel to the pivot axis, the cross bar extending between the first support and the second support and outwardly offset from the second side of the lever body.

2. The instrument of claim 1, wherein the gripping section forms a tubular extension having an opening for receiving the exterior of a spinal implant.

3. The instrument of claim 2 comprising a handle end coupled to the gripping section, the handle end moveable between a closed setting, in which the opening has a first size, and an open setting, in which the opening has a second size that is larger than the first size.

4. The instrument of claim 1, wherein the second support includes a bore sized to receive the cross bar.

5. The instrument of claim 1, wherein the lever body includes a first lever arm and a second lever arm coupled with the first lever arm, the first lever arm comprising a first gripping extension, and the second lever arm comprising a second gripping extension.

6. The instrument of claim 5, wherein the lever body comprises at least one spring element engaging the first and second gripping extensions, said at least one spring element retaining the first and second gripping extensions in a symmetrical arrangement relative to one another to keep the first and second gripping extensions oriented at the same angle with respect to the lever body.

7. An instrument for manipulating a spinal fixation rod, the instrument comprising:
  a gripping section for engaging a spinal implant;
  a lever body pivotally attached to the gripping section on a pivot axis, the lever body comprising a first side and a second side opposite the first side; and
  a rod carrier extending from the lever body,
  the lever body comprising a first lever arm and a second lever arm separated from the first lever arm by a gap, and the gripping section comprising a first gripping extension pivotally coupled with the first lever arm, and a second gripping extension pivotally coupled with the second lever arm, the gripping section extending from the first side of the lever body,
  the rod carrier comprising a first support extending outwardly from the second side of the lever body and a second support extending outwardly from the second side of the lever body generally parallel to the first support,
  the first support comprising a cross bar having a longitudinal cross bar axis extending generally parallel to the pivot axis, the cross bar extending between the first support and the second support and outwardly offset from the second side of the lever body.

8. The instrument of claim 7, wherein the gripping section forms a tubular extension having an opening for receiving the exterior of a spinal implant.

9. The instrument of claim 8 comprising a handle end coupled to the gripping section, the handle end moveable between a closed setting, in which the opening has a first size, and an open setting, in which the opening has a second size that is larger than the first size.

10. The instrument of claim 9, wherein the handle end comprises a pair of scissor handles.

11. The instrument of claim 10 comprising a ratchet connection between the scissor handles to releasably lock the relative position of the scissor handles.

12. The instrument of claim 9, wherein the lever body comprises at least one spring element engaging the first and second gripping extensions, said at least one spring element retaining the first and second gripping extensions in a symmetrical arrangement relative to one another to keep the first and second gripping extensions oriented at the same angle with respect to the lever body.

13. The instrument of claim 7, wherein the second support forms a bore sized to receive the cross bar.

14. The instrument of claim 7, wherein the first and second gripping sections are separated by a rod-receiving channel.

15. The instrument of claim 14, wherein the cross bar extends generally perpendicularly to the rod-receiving channel.

16. An instrument for manipulating a spinal fixation rod, the instrument comprising:
  a gripping section for engaging a spinal implant;
  a lever body pivotally attached to the gripping section on a pivot axis, the lever body comprising a first side and a second side opposite the first side;
  a rod carrier extending from the lever body; and
  a handle end operable to displace the gripping section between an open position and a closed position, the handle end also being operable to pivot the lever body relative to the gripping section,
  the rod carrier comprising a first support extending outwardly from the first side of the lever body and a second support extending outwardly from the second side of the lever body generally parallel to the first support,
  the first support comprising a cross bar having a longitudinal cross bar axis extending generally parallel to the pivot axis, the cross bar extending between the first support and the second support and outwardly offset from the second side of the lever body.

17. The instrument of claim 16, wherein the gripping section forms a tubular extension having an opening for receiving the exterior of a spinal implant.

18. The instrument of claim 17, wherein the opening has a first size when the gripping section is in the closed position, and the opening has a second size when the gripping section is in the open position, the second size being larger than the first size.

19. The instrument of claim 16, wherein the gripping section comprises a first gripping extension and a second gripping extension arranged in a symmetrical relationship with the first gripping extension.

20. The instrument of claim 16, wherein the lever body includes a first lever arm and a second lever arm coupled with the first lever arm, the first lever arm comprising a first gripping extension, and the second lever arm comprising a second gripping extension.

* * * * *